United States Patent [19]

Cohrs et al.

[11] Patent Number: 4,674,317

[45] Date of Patent: Jun. 23, 1987

[54] APPARATUS FOR DETERMINING THE FLOW CHARACTERISTIC OF A VOLUMETRIC FLOWMETER

[75] Inventors: Gary D. Cohrs, Tempe; Edward E. Francisco, Jr., Paradise Valley, both of Ariz.

[73] Assignee: Flow Technology, Phoenix, Ariz.

[21] Appl. No.: 843,001

[22] Filed: Mar. 24, 1986

Related U.S. Application Data

[62] Division of Ser. No. 757,272, Jul. 19, 1985, Pat. No. 4,627,267.

[51] Int. Cl.$^4$ ............................................. G01F 25/00
[52] U.S. Cl. ......................................................... 73/3
[58] Field of Search ................ 73/3; 33/DIG. 3; 91/5

[56] References Cited

U.S. PATENT DOCUMENTS

| | | |
|---|---|---|
| 3,098,382 | 7/1963 | Hoffman et al. |
| 3,492,856 | 2/1970 | Francisco, Jr. |
| 3,631,709 | 1/1972 | Smith et al. ................................. 73/3 |
| 4,037,325 | 7/1977 | Weber et al. ................ 33/DIG. 3 X |
| 4,152,922 | 5/1979 | Francisco, Jr. |
| 4,372,147 | 2/1983 | Waugh et al. |

FOREIGN PATENT DOCUMENTS

| | | |
|---|---|---|
| 8019337 | 7/1980 | Fed. Rep. of Germany. |
| 1033739 | 6/1966 | United Kingdom ...................... 91/5 |
| 679810 | 8/1979 | U.S.S.R. ..................................... 73/3 |

OTHER PUBLICATIONS

Brooks Technical Bulletin, Repeatability Tests on 12" Brooks Compact Prover., Jun. 1982.

Flow: Its Measurement and Control in Science and Industry, vol. 2, Instrument Society of America, 1981.

*Primary Examiner*—Jerry W. Myracle
*Attorney, Agent, or Firm*—Christie, Parker & Hale

[57] ABSTRACT

A mechanical displacement flowmeter calibrator has a first fluid line external of the measuring cylinder of the calibrator connected between the inlet and outlet thereof. A flow meter that produces flow-representative pulses is connected in the fluid line. A rod is connected to a measuring piston adapted to travel through the measuring cylinder as a fluid barrier. The rod drives the measuring piston through the measuring cylinder at a predetermined, constant speed and thereby determines the flow rate of the calibration. The displacement of the measuring piston is sensed as it travels through the measuring cylinder during a test run, while the pulses produced by the flowmeter are counted during the time interval in which the piston displaces a given volume. The flowmeter is preferably connected in the fluid line at the pressure null point. First and second annular edge seals around the periphery of the measuring piston form an annular cavity into which pressurized fluid, preferably a lubricant, is injected. Before a test run, fluid flow in a second fluid line, external of the measuring cylinder, is induced, thereby establishing a closed loop around the first and second fluid lines and the measuring cylinder. To initiate a test run, fluid flow through the second fluid line is blocked to operate the measuring piston. Simultaneously therewith, the measuring piston is driven through the measuring cylinder from end-to-end to execute a test run.

15 Claims, 5 Drawing Figures

APPARATUS FOR DETERMINING THE FLOW CHARACTERISTIC OF A VOLUMETRIC FLOWMETER

This is a division of application Ser. No. 06/757,272 filed July 19, 1985, now U.S. Pat. No. 4,627,267.

BACKGROUND OF THE INVENTION

This invention relates to the measurement of fluid flow and, more particularly, to the determination of the flow characteristic of a flowmeter.

In order to obtain accurate readings from a flowmeter, it must be calibrated from time to time by determining its characteristic, i.e., the constant of proportionality between the flow rate of the fluid flowing through the flowmeter and the response given by the flowmeter, sometimes called the K-factor of the flowmeter. In the case of a turbine type flowmeter that develops electrical oscillations proportional in number to the volume of flow through the flowmeter, this characteristic is expressed in terms of the number of pulses generated by the flowmeter per unit volume of fluid passing there through. The flowmeter characteristic is a function of the type of fluid, as well as the fluid temperature, pressure, and flow rate, and varies as the parts of the flowmeter wear in the course of use. Apparatus to determine the characteristic of a flowmeter while in an operating fluid system called a prover. Apparatus to determine the characteristic of a flowmeter in a self-contained system, i.e., not in an operating fluid system, is called a calibrator.

My U.S. Pat. No. 4,152,922 discloses a small-volume prover that employs mechanical volume displacement techniques. The prover has a measuring piston that travels through a measuring cylinder as a fluid barrier in synchronism with fluid passing through the operating fluid system that includes the flowmeter under test. A rod connects the measuring piston to a fluidically actuated control piston in a control cylinder which serves to hold the measuring piston at the upstream end of the measuring cylinder between test runs and return the measuring piston to the upstream end of the measuring cylinder after each test run. When the measuring piston is released at the upstream end of the measuring cylinder to start a test run, the momentum of the fluid flowing through the system rapidly accelerates the measuring piston to the same speed as the fluid flowing through the measuring cylinder, which is representative of the flow rate passing through the flowmeter. The K-factor is determined by counting the number of pulses produced by the flowmeter during the time interval of a given volumetric displacement of the measuring piston.

Although the state-of-the-art of low-volume mechanical displacement provers has rapidly advanced in recent years, the development of small-volume calibrators has not kept pace. The large fluid volume requirements often make it impractical to duplicate the actual conditions, i.e., pressure, temperature, and fluid type, in the operating system of the flowmeter, so the K-factor must be derived inferentially. In small-volume operation, drag represented the friction of the measuring piston and leakage across the measuring piston adversely affect the accuracy and repeatablilty of the measurements. When the fluid is gas, these adverse effects are exacerbated by the compressibility of gas. Compressibility also makes it difficult to control the pressure of a gas passing through the flowmeter under test.

SUMMARY OF THE INVENTION

According to one aspect of the invention, a mechanical displacement flowmeter calibrator has a fluid line external of the measuring cylinder of the calibrator connected between the inlet and outlet thereof. A flowmeter that produces flow-representative pulses is connected in the fluid line. A rod is connected to a measuring piston adapted to travel through the measuring cylinder as a fluid barrier. The displacement of the measuring piston is sensed as it travels through the measuring cylinder during a test run, while the pulses produced by the flowmeter are counted during the time interval in which the piston displaces a given volume. Responsive to the sensed displacement of the measuring piston, the rod is controlled to drive the measuring piston through the measuring cylinder at a predetermined, constant speed, which determines the flow rate of the calibration. Because the calibrator has a small fixed volume, the pressure and temperature of the fluid passing through the flowmeter can be closely controlled, and any type of test fluid can be used irrespective of cost. Thus, the pressure, temperature, and type of test fluid, can be selected so as to duplicate the actual conditions of the flowmeter in its operating system. Moreover, the flow rate can be closely controlled by regulating the driving speed of the rod.

BRIEF DESCRIPTION OF THE DRAWINGS

The features of specific embodiments of the best mode contemplated of carrying out the invention are illustrated in drawings, in which.

DETAILED DESCRIPTION OF THE SPECIFIC EMBODIMENTS

Figure 1:
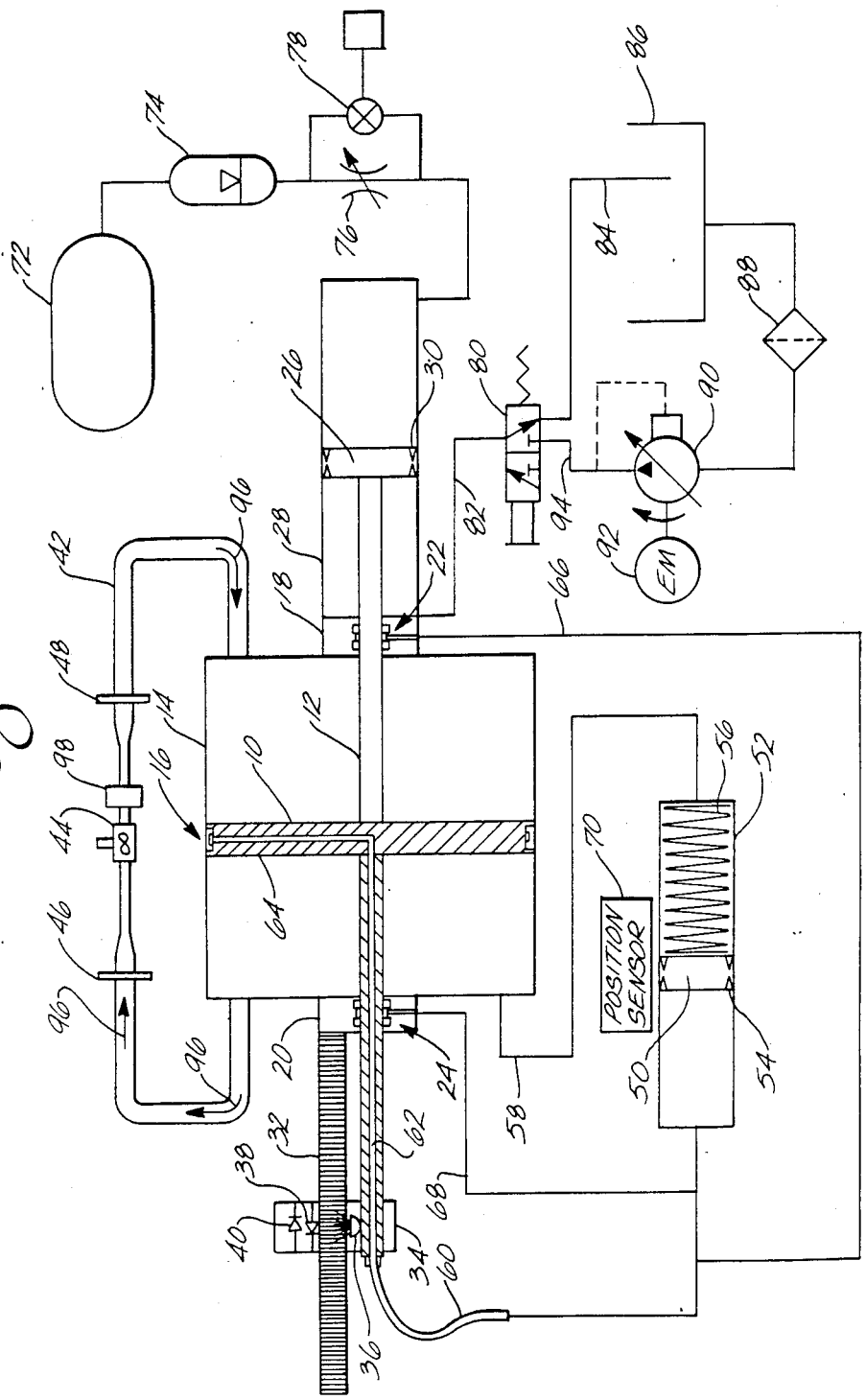
FIG. 1 is a schematic diagram of one embodiment of a calibrator incorporating principles of the invention.

In FIG. 1, a measuring piston 10 mounted on a rod 12 is adapted to travel through a measuring cylinder 14 from end-to-end. A double annular seal 16 described in detail below in connection with FIG. 2, extends around the peripheral edge of measuring piston 10 to form an annular cavity. A seal housing 18 is mounted on the upstream end of measuring cylinder 14 and a seal housing 20 is mounted on the downstream end of measuring cylinder 14. Double annular seals 22 and 24 are installed in housings 18 and 20, respectively, around rod 12. Measuring piston 10 travels through measuring cylinder 14 as a fluid barrier.

A control piston 26 is connected to the upstream end of rod 12. Control piston 26 travels through a control cylinder 28 mounted on the end of seal housing 18 as measuring piston 10 travels through measuring cylinder 14. Control piston 26 has a peripheral edge seal 30 shown schematically.

At the downstream end of measuring cylinder 14, a linear optical encoder serves as a measuring piston displacement sensor for measuring piston 10. The optical encoder comprises a stationary transparent elongated ruler 32 with opaque graduations mounted on the end of seal housing 20 parallel to rod 12 and an optical transducer 34 mounted on the upstream end of rod 12. Optical transducer 34, (which is a conventional off-the-shelf piece of equipment), comprises a light source 36 and light-detecting diodes 38 and 40. By way of example, optical transducer 34 could comprise Linear Optical Encoder DRC 1200 sold by Dynamics Research of Wilmington, Mass.

Measuring cylinder 14 has an inlet at one end and an outlet at the other end connected externally by a fluid line 42. Preferably, line 42 approximately follows the shortest path between the inlet and outlet of measuring cylinder 14, as shown, to minimize space requirements.

A flowmeter 44 to be calibrated, such as a turbine meter, is connected in fluid line 42. Fluid line 42 has fittings 46 and 48, which permits the installation of different flowmeters for calibration purposes. In any case, to insure stable flow conditions in the flowmeter under test, the distance between fittings 46 and 48 is about thirty times the diameter of the section of the fluid line therebetween, which depends upon the flow rating of the flowmeter under test.

An accumulator has a piston 50 that travels through a cylinder 52 as a fluid barrier. Piston 50 has a schematically represented peripheral edge seal 54. A compression spring 56 is disposed between an inlet end of cylinder 52 and piston 50 to urge piston 50 toward an outlet end of cylinder 52. Measuring cylinder 14 is connected to the inlet end of cylinder 52 by a fluid line 58. The outlet end of cylinder 52 is also connected by a fluid line 60, an axial bore 62 through the downstream end of rod 12, and a radial bore 64 through measuring piston 10 to the annular cavity around the periphery of measuring piston 10. The outlet end of cylinder 52 is also connected to the annular cavities formed in seal housings 18 and 20, respectively, by fluid lines 66 and 68, respectively. The space between piston and the outlet end of cylinder 52 is filled with a liquid lubricant, such as light lubricating oil. A spring 56 pressurizes the liquid lubricant, which is distributed to the annular cavities formed by seals 16, 22, and 24. The liquid lubricant is at a higher pressure than the fluid in measuring cylinder 14. As the pressure of the fluid in measuring cylinder 14 changes, the force on piston 50, and thus the pressure of the liquid lubricant changes accordingly to maintain an approximately constant pressure differential between the liquid lubricant and the fluid in measuring cylinder 14. The liquid lubricant serves to reduce the frictional drag of measuring piston 10 and rod 12 as piston 10 travels through measuring cylinder 14 and the liquid lubricant pressure prevents liquid lubricant prevents leakage of the fluid in measuring cylinder 14 across measuring piston 10 and to the exterior of measuring cylinder 14. A position sensor 70 which could be mechanical, optical, or magnetic in nature, indicates the position of piston 50. A failure of seal 16, 22, or 24 occurs when position sensor 70 indicates a steady movement of piston 50 toward the outlet end of cylinder 52.

A plenum chamber 72 having a volume much larger, i.e., 200 times or more, than control cylinder 28, is charged with a pressurized gas. Plenum chamber 72 is connected to the top of a hydraulic accumulator 74. The bottom of accumulator 74 is connected by a throttling valve 76 to the upstream end of control cylinder 28 to supply hydraulic fluid to the upstream face of control piston 26. A normally closed solenoid valve 78 is connected in parallel with throttling valve 76 to provide a bypass thereto. The setting of throttling valve 76, which applies force to the upstream face of piston 26, determines the speed of measuring piston 10, after equilibrium has been achieved. The speed of measuring piston 10, in turn, determines the volumetric flow rate of the test fluid passing through flowmeter 44. Throttling valve 76 may be manually set or may be controlled automatically by a servo loop in response to the linear encoder. The described apparatus permits calibration of the flowmeter under test at a series of precisely determined volumetric flow rates. A three-port, two-position solenoid actuated valve 80 controls piston return after a test run. One port is connected by a fluid line 82 to the downstream end of control cylinder 28. Another port is connected by a fluid line 84 to a reservoir 86 for hydraulic fluid. Reservoir 86 is connected by a filter 88 to the inlet of a constant pressure variable displacement pump 90, which is driven by an electric motor 92. The outlet of pump 90 is connected by a fluid line 94 to the remaining port of valve 80. Pump 90 produces a pressure greater than the pressure in plenum 72. Measuring cylinder 14 and fluid line 42 are charged with the test fluid to a predetermined pressure. The features of the invention can be used to particular advantage in calibrating a flowmeter with a gas as the test fluid, although the invention can also be used to advantage with a liquid as the test fluid, particularly if temperature uniformity is an important factor.

In operation, a test run begins with measuring piston 10 at the upstream end of measuring cylinder 14 and control piston 26 at the upstream end of control cylinder 28 (extreme right position as viewed in FIG. 1). Valve 78 is closed and valve 80 is in the position that supplies hydraulic fluid at constant pressure to the downstream face of control piston 26. Before initiating a test run, throttle valve 76 is set to the desired flow rate for calibration. To initiate a test run, the position of valve 80 is changed, thereby depressurizing the downstream face of control piston 26. As a result, the pressure exerted on the upstream face of control piston 26 by the hydraulic fluid from accumulator 74 drives measuring piston 10 from the upstream end of measuring cylinder 14 to the downstream end thereof. As this occurs, the hydraulic fluid downstream of control piston 26 flows through valve 80 into reservoir 86 and the test fluid in measuring cylinder 14 flows through flowmeter 44 in the direction indicated by arrows 96. As measuring piston 10 displaces a given volume in measuring cylinder 14 determined by the measuring piston displacement sensor, the number of pulses generated by flowmeter 44 is counted. The result in volume per pulse is the K-factor of flowmeter 44. Preferably, the double chronometry technique described in my U.S. Pat. No. 3,403,544, is employed to make this count.

As shown, fluid line 42 is preferably symmetrically configured with respect to the inlet and outlet ends of measuring cylinder 14. It has been discovered that such an external fluid line has a pressure null point along its length, essentially at the midpoint thereof, assuming symmetry as described, at which no pressure changes occur due to the compressibility of the test fluid in measuring cylinder 14. Flowmeter 44 is located in fluid line 42 at the pressure null point so that calibration of flowmeter 44 occurs at a constant pressure despite the fact that the pressure upstream and downstream of measuring piston 10 may vary due to compressibility. To fine tune fluid line 42 and thus make the pressure null point precisely coincide with the turbine of flowmeter 44 after flowmeter 44 is installed in fluid line 42, an orifice 98 such as an orifice plate or an adjustable valve could be connected in fluid line 42 near flowmeter 44. Such an orifice compensates for deviations in symmetry that may occur due to tolerances in the dimensions of fluid line 42. This feature is also applicable to a ball calibrator.

In a typical embodiment of the invention, the length of measuring cylinder 14 from end-to-end is sufficient for pistons 10 and 26 to have a 48 inch stroke and the inside diameter of measuring cylinder 14 is 12 inches. The typical range of flow rates for such a calibrator is 0.03 to 60 actual cubic feet of test fluid per minute.

Figure 2:
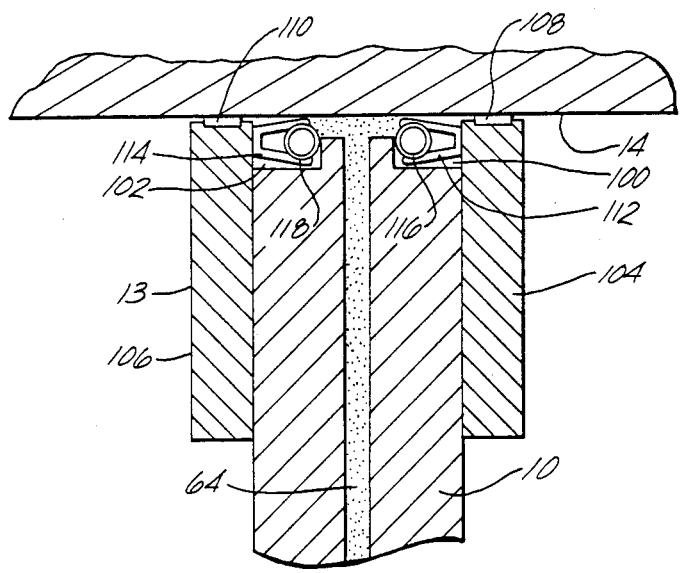
FIG. 2 is an enlargement of a portion of the embodiment of FIG. 1 illustrating the double annular seal on the peripheral edge of the measuring piston.

In FIG. 2, the peripheral edge of measuring piston 10 has a groove 100 opening toward the upstream end of measuring cylinder 14 and a groove 102 opening toward the downstream end of cylinder 14. Annular retaining plates 104 and 106 having an outer diameter slightly smaller than the inner diameter of measuring cylinder 14 are secured to the upstream and downstream faces of measuring piston 10, respectively. Annular support rings 108 and 110 protrude slightly from the outer periphery of retaining plates 104 and 106, respectively, to provide a bearing surface that supports piston 10 with a snug fit in measuring cylinder 14. Rings 108 and 110 could be formed from Rulon tape wrapped around the outer periphery of retaining plates 104 and 106. The periphery of measuring piston 10 between grooves 100 and 102 is spaced from the inner surface of measuring cylinder 14 to provide fluid communication from bore 64 to grooves 100 and 102. U-shaped annular lip seals 112 and 114, which are retained in grooves 100 and 102, respectively, have legs that face toward each other and bases that face away from each other. Seal expanders 116 and 118, which are disposed within lip seals 112 and 114, respectively, spread their legs apart to bear against the inner surface of measuring cylinder 14 and the base of grooves 100 and 102, respectively. The liquid lubricant under pressure, represented by stipling in (FIG. 2, further) tends to spread the legs of lip seals 112 and 114 apart so as to prevent leakage of test fluid across piston 10. By way of example, lip seals 112 and 114 could be teflon loaded with Rulon fiber for strength and wear and seal expanders 116 and 118 could be non-corrosive stainless steel garter springs. A suitable double annular seal as illustrated in FIG. 2 is sold by Balseal of Santa Monica, Calif., Model No. 307A-11.75-G.

Seals 22 and 24 are essentially the same as seal 16 with the exception that the components of the seal are mounted on the stationary members, i.e., seal housings 18 and 20, rather than the movable member, i.e., measuring piston 10. Thus, each seal housing has a pair of spaced apart annular grooves, as grooves 100 and 102, in which U-shaped lip seals, as lip seals 112 and 114, with inwardly facing legs urged apart by seal expanders, as seal expanders 116 and 118, are disposed. Annular support rings, as support rings 108 and 110, extend into the rod-receiving bore to provide bearing surfaces for the rod. The fluid line (66 or 68) leads into an annular cavity, as radial bore 64, formed by the grooves and a recess therebetween.

Figure 3:
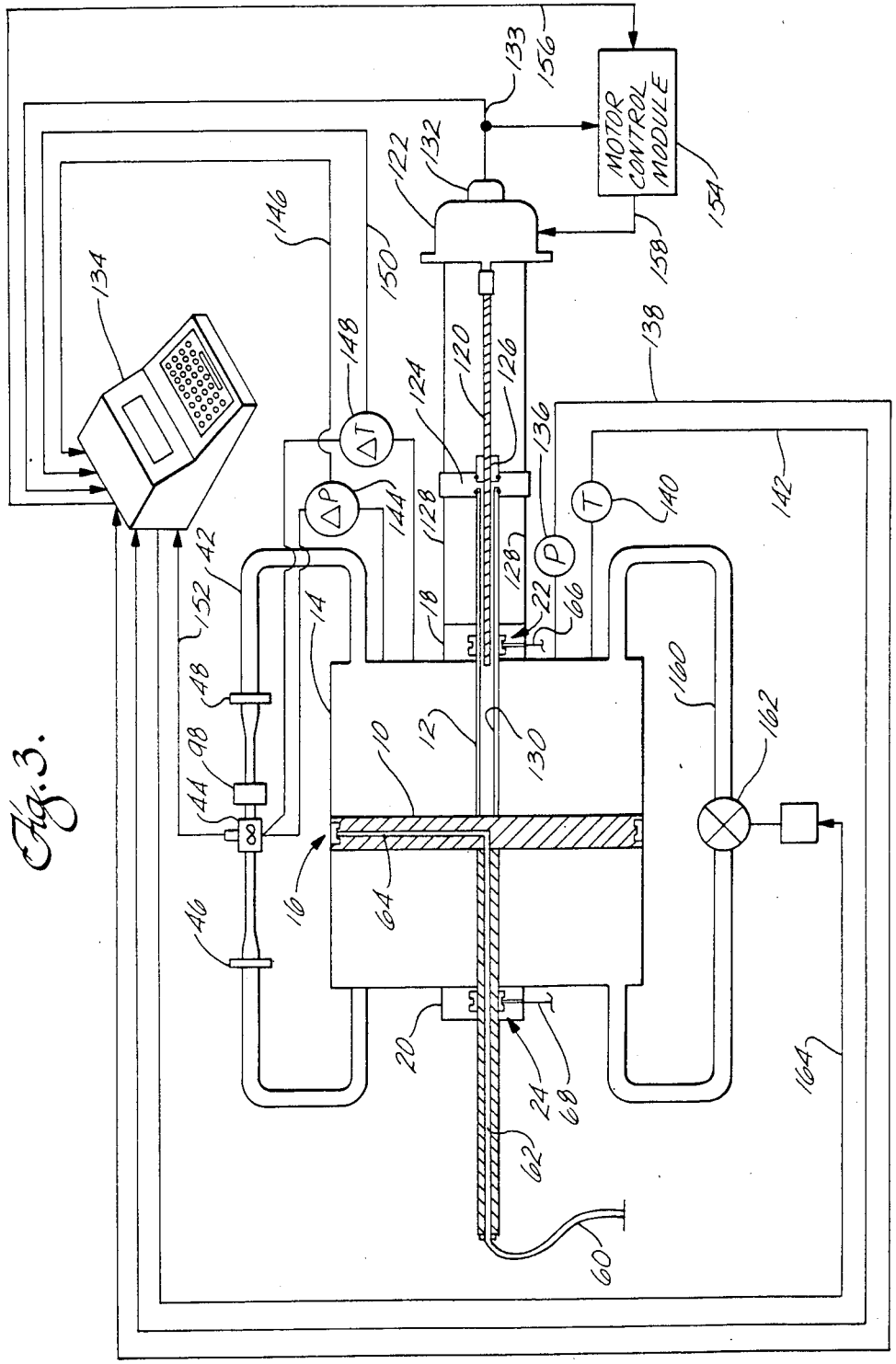
FIG. 3 is a schematic diagram of another embodiment of a calibrator incorporating principles of the invention.

In the embodiment of FIG. 3, the components in common with the embodiment of FIG. 1 bear the same reference numerals. Instead of driving measuring piston fluidically as shown in FIG. 1, measuring piston 10 is driven mechanically in this embodiment. Specifically, a threaded shaft 120 is rotatably driven by a motor 122. The threads of shaft 120 engage threads at 126 on a translatable, non-rotatable carriage 124, which is fixedly mounted on the downstream end of rod 12. Carriage 124 rides on rails 128. The upstream end of rod 12 has a bore 130 that receives the portion of shaft 120 that extends beyond the threaded engagement at 126. A rotary encoder 132 is coupled to shaft 120, to serve as a measuring piston displacement sensor. The output of encoder 132 is connected to a control console 134 by an electrical cable 133. The output of a pressure transducer 136, which senses the pressure in measuring cylinder 14, is connected to console 134 by an electrical cable 138. The output of a temperature transducer 140, which senses the temperature of the fluid in measuring cylinder 14, is connected to console 134 by an electrical cable 142. The output of a P transmitter 144, which senses the fluid pressure difference between flowmeter 44 and measuring cylinder 14 is connected to console 134 by an electrical cable 146. A T transducer 148, which senses the fluid temperature difference between flowmeter 44 and measuring cylinder 14, is connected to console 134 by an electricalcable 150. On the basis of the data transmitted to console 134 by cable 133, electronics in console 134 generates an error rate control signal, which is applied to a motor control module 154 by an electrical cable 156. Motor control module 154 derives an actuating voltage for motor 122 responsive to the error rate control signal from console 134. This control signal is applied to the actuating winding of motor 122 by an electrical cable 158. As a result, motor 122 drives measuring piston 10 at a predetermined constant speed from the upstream end to the downstream end of measuring cylinder 14 in the course of a test run to produce the data for deriving the K-factor of flowmeter 44, which is transmitted to console 134 by cables 133, 138, 142, 146, 150, and 152. By way of example motor 122 could be a three phase synchronous motor and control module 154 could generate a three phase actuating voltage, the frequency of which varies as a function of the error rate control signal; motor 122 could be Model MC 345 sold by PMI Motors of Syosset, New York and control module 154 could be Model DMC 100 sold by Galil Motur Control, Mountain View, Calif. Although not shown, this embodiment also employs accumulator piston 50, cylinder 52, spring 56, and fluid line 58 of FIG. 1.

A fluid line 160 is connected external of measuring cylinder 14 between its ends. A normally closed solenoid-actuated valve 162 is disposed in line 160. Line 160 preferably has a much larger diameter than line 42 so that most of the fluid passes therethrough when measuring piston 10 is returned to the upstream end of measuring cylinder 14 at the end of a test run. Console 134 is connected to the solenoid of valve 162 by an electrical cable 164. When the electronics in console 134 detect the arrival of measuring piston 10 at the downstream end of measuring cylinder 14, valve 162 is opened and motor 122 drives measuring piston 10 back to the upstream end of measuring cylinder 14 in preparation for another test run. The output of encoder 132 is also connected to motor control module to indicate when measuring piston 10 is at the upstream or downstream end of measuring cylinder 14.

The mechanical measuring piston driving arrangement of FIG. 3 and the fluidic measuring piston driving arrangement of FIG. 1 are interchangeable. Thus, if desired, the fluidic measuring piston driving arrangement of FIG. 1 could be substituted for the mechanical measuring piston driving arrangement of FIG. 3 and visa versa.

Figure 4:
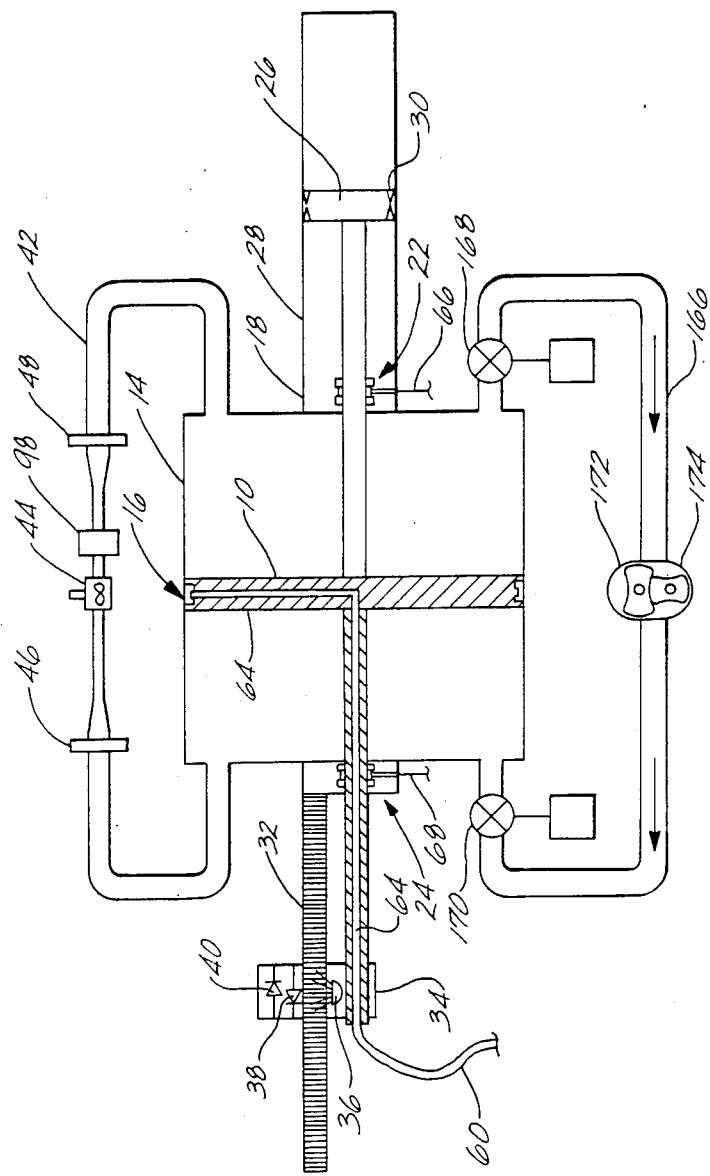
FIG. 4 is a schematic diagram of still another embodiment of a calibrator incorporating principles of the invention.

In the embodiment of FIG. 4, like components are identified with the same references numerals as the embodiments of FIGS. 1 and 3. A fluid line 166 is connected external of measuring cylinder 14 from one end thereof to the other. Preferably line 166 has a substantially larger cross section than line 42. A normally open solenoid-actuated valve 168 is disposed in line 166 near the upstream end of measuring cylinder 14, a normally open solenoid-actuated valve 170 is disposed in line 166 near the downstream end of measuring cylinder 14, and a flow inducer pump 174 is disposed in line 166 between valves 168 and 170. It is assumed that control piston 26 is driven and returned by the same fluidic driving arrangement shown in FIG. 1, although the mechanical driving arrangement could be used. Between test runs, valves 168 and 170 are open and measuring piston 10 is disposed at the upstream end of measuring cylinder 14. Pump 174 induces the test fluid to flow through line 166, measuring cylinder 14, and line 42 at the approximate flow rate at which flowmeter 44 is to be calibrated. It is to be noted, however, that pump 174 does not determine the flow rate of calibration—the driving speed of rod 12 does. To initiate a test run, valves 168 and 170 are closed to remove pump 174 from the test fluid circuit, and simultaneously therewith control piston 26 is actuated to drive measuring piston 10 through measuring cylinder 14 at the prescribed speed to establish the desired flow rate through flowmeter 44. (Actually, it may be desirable in practice to anticipate the closing off of line 166 by starting to drive measuring piston 10 a few milliseconds before closing valves 168 and 170). In this embodiment, the test fluid is in motion at the time that a test run is initiated and, therefore, flowmeter 44 can attain steady-state operation more rapidly than the embodiment of FIG. 1. This embodiment is especially useful in calibrating a positive displacement meter, which responds slowly to changes in flow rate, and is also applicable to ball calibrators.

The details of construction for the calibrators of FIGS. 1, 3, and 4 are described in my following U.S. patents, the disclosures of which are incorporated fully herein by reference: U.S. Pat. Nos. 3,403,544, which issued on Oct. 1, 1968; 3,492,856, which issued on Feb. 3, 1970; and 4,152,922, which issued on May 8, 1979. For a volume of about 3 cubic feet, a typical maximum piston speed in the embodiments of FIGS. 1 and 3 is about 2 feet per second and in the embodiment of FIG. 4 is about 4 to 5 feet.

Figure 5:
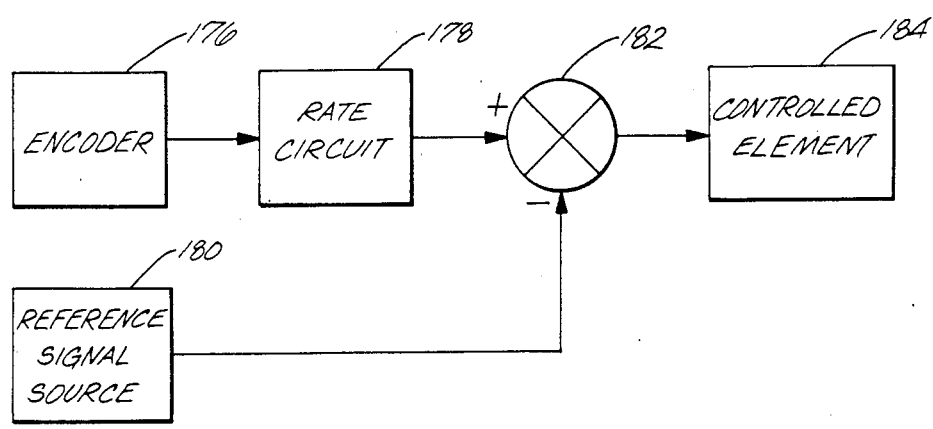
FIG. 5 is a block diagram of apparatus for driving the measuring piston during a test run.

FIG. 5 represents the system for controlling the speed of measuring piston 14, either fluidically, as shown in FIG. 1, or mechanically, as shown in FIG. 2. The output of an encoder 176, which could be the optical encoder of FIG. 1 or the rotary encoder of FIG. 2, is applied to a rate circuit 178 located in console 134. The output of rate circuit 178 represents the actual speed of measuring piston 10. The output of a reference signal source 180 in console 134 and the output of rate circuit 178 are applied to a summing junction 182 in console 134. The output of summing junction 182 is applied to a controlled element 184, which in the embodiment of FIG. 1 is the servo actuator for valve 76 and in the embodiment of FIG. 2 is motor control module 154. Thus, the controlled element drives measuring piston 10 at a constant speed prescribed by reference signal source 180, thereby establishing a constant predetermined flow rate through the flowmeter under test.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention. Although the invention can be used to particular advantage to calibrate turbine meters or other volumetric flowmeters, it can also be used to calibrate other types of flowmeters.

What is claimed is:

1. A flowmeter calibrator comprising:
    a fluid displacement measuring cylinder having at its respective ends an inlet and an outlet;
    a fluid displacement measuring pistion adapted to travel through the measuring cylinder as a fluid barrier;
    means for sensing the displacement of the measuring piston as it travels through the measuring cylinder;
    a fluid line external of the measuring cylinder connected between the inlet and outlet thereof;
    a flowmeter connected in the fluid line, the flowmeter producing flow representative pulses;
    a rod connected to the measuring piston;
    means connected to the rod for driving the measuring pistion through the measuring cylinder;
    means responsive to the sensing means for controlling the driving means to drive the measuring piston through the measuring cylinder at a predetermined constant speed; and
    means for counting the pulses produced by the flowmeter during a given displacement of the measuring piston at the constant speed.

2. The calibrator of claim 1 in which the driving means comprises a control cylinder, a control piston connected to the rod and movable through the control cylinder, means for sensing the speed of the measuring piston, and means responsive to the sensing means for controlling the pressure difference across the control piston to maintain the predetermined constant speed.

3. The calibrator of claim 2 in which the sensing means comprises a linear optical encoder.

4. The calibrator of claim 3 in which the linear optical encoder comprises a stationary, transparent, elongated ruler with opaque graduations mounted on the measuring cylinder adjacent to the rod and an optical transducer mounted on the rod to sense the graduations of the ruler.

5. The calibrator of claim 2 in which the means for controlling the pressure difference across the control piston comprises a gas filled plenum having a substantially larger volume than the control cylinder, means for connecting the gas pressurized plenum to one end of the control cylinder, a source of hydraulic fluid connected to the other end of the control cylinder, and means for controlling the pressure of the hydraulic fluid responsive to the sensing means.

6. The calibrator of claim 1 in which the driving means comprises an electric motor, means for coupling the electric motor to the rod, means for sensing the speed of the measuring piston, and means responsive to the sensing means for controlling the speed of the motor to maintain the predetermined constant speed.

7. The calibrator of claim 6 in which the coupling means comprising a threaded shaft connected at one end to the motor, and a translatable non-rotatable carriage mounted on the rod and having threads that engage the threaded shaft such that as the threaded shaft rotates the carriage translates.

8. The calibrator of claim 7 in which the sensing means comprises a rotary encoder coupled to the shaft.

9. The calibrator of claim 1 in which the fluid line has a pressure null point along its length and the flowmeter is connected in the fluid line at the pressure null point.

10. The calibrator of claim 9 in which the line approximately follows the shortest path between the inlet and the outlet of the measuring cylinder.

11. The calibrator of claim 9 in which the line includes an orifice in the line near to the flowmeter to shift the pressure null point.

12. The calibrator of claim 11 in which the orifice is an orifice plate.

13. The calibrator of claim 11 in which the orifice is an adjustable valve.

14. The flowmeter claibrator of claim 1 additionally comprising means responsive to the sensing means and the counting means for generating a representation of the K-factor of the flowmeter.

15. The flowmeter claibrator of claim 1, in which the controlling means comprises means for generating a signal representative of the actual speed of the measuring piston, a reference signal source representative of the desired speed of the measuring piston, a summing junction to which the reference signal and the actual speed representative signal are applied, and means for connecting the summing junction to the driving means.

* * * * *